US009808157B2

(12) United States Patent
Pletcher et al.

(10) Patent No.: US 9,808,157 B2
(45) Date of Patent: Nov. 7, 2017

(54) HANDS-FREE INTERFACE

(71) Applicant: Verily Life Sciences LLC, Mountain View, CA (US)

(72) Inventors: Nathan Pletcher, Mountain View, CA (US); Andrew Nelson, Richmond, CA (US); Francis Honore, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 319 days.

(21) Appl. No.: 14/143,070

(22) Filed: Dec. 30, 2013

(65) Prior Publication Data

US 2015/0182116 A1    Jul. 2, 2015

(51) Int. Cl.
*G06F 3/02* (2006.01)
*A61B 5/00* (2006.01)
*A61B 5/145* (2006.01)
*A61B 5/1468* (2006.01)
*G06F 3/01* (2006.01)

(52) U.S. Cl.
CPC .......... *A61B 5/0026* (2013.01); *A61B 5/1468* (2013.01); *A61B 5/14532* (2013.01); *A61B 5/14546* (2013.01); *A61B 5/6821* (2013.01); *G06F 3/013* (2013.01); *G06F 3/017* (2013.01); *A61B 2560/0204* (2013.01); *A61B 2560/0487* (2013.01)

(58) Field of Classification Search
CPC .............. A61B 5/0026; A61B 5/14532; A61B 5/14546; A61B 5/1468; A61B 5/6821; G06F 3/013; G06F 3/017
USPC ....................................................... 250/221
See application file for complete search history.

(56) References Cited

U.S. PATENT DOCUMENTS

| 4,995,083 | A | * | 2/1991 | Baker | .................. | H04M 1/727 |
| | | | | | | 375/365 |
| 6,920,283 | B2 | | 7/2005 | Goldstein | | |
| RE39,539 | E | * | 4/2007 | Torch | ................... | A61B 3/0066 |
| | | | | | | 340/573.1 |
| 2005/0036109 | A1 | | 2/2005 | Blum et al. | | |
| 2012/0245444 | A1 | | 9/2012 | Otis et al. | | |
| 2012/0281181 | A1 | | 11/2012 | Chen | | |
| 2013/0135578 | A1 | | 5/2013 | Pugh et al. | | |
| 2013/0222271 | A1 | | 8/2013 | Alberth | | |

(Continued)

FOREIGN PATENT DOCUMENTS

EP    1760515 A2    3/2007
WO    2012136431 A1    10/2012

OTHER PUBLICATIONS

International Search Report and Written Opinion of International Application No. PCT/US2014/061115 dated Jan. 16, 2015 (mailed Jan. 19, 2015).

*Primary Examiner* — Renee Chavez
(74) *Attorney, Agent, or Firm* — McDonnell Boehnen Hulbert & Berghoff LLP

(57) ABSTRACT

A wearable device and external reader is provided for herein. In some embodiments of the present disclosure, the wearable device or the reader is configured to receive a level of radiant energy, detect a change in the received level of radiant energy, determine that the detected change in the received level of radiant energy is indicative of a predetermined pattern of received radiant energy, and responsively operate (or cause to be operated via the external reader) one or more external devices.

22 Claims, 9 Drawing Sheets

(56) References Cited

U.S. PATENT DOCUMENTS

| | | |
|---|---|---|
| 2013/0257709 A1 | 10/2013 | Raffle et al. |
| 2013/0258287 A1 | 10/2013 | Pugh et al. |
| 2014/0016097 A1* | 1/2014 | Leonardi ............. A61B 3/0041 351/209 |

* cited by examiner

HANDS-FREE INTERFACE

BACKGROUND

Unless otherwise indicated herein, the materials described in this section are not prior art to the claims in this application and are not admitted to be prior art by inclusion in this section.

One type of wearable device has control electronics and an antenna embedded therein. An external reader may be configured to transmit radio frequency (RF) energy to the wearable device so as to provide power to the wearable device. The combination of the control electronics and the antenna may be configured to receive such RF energy transmitted by the external reader and modify the impedance of the antenna so as to characteristically modify the backscatter from the antenna. In this way, the wearable device may communicate back to external reader.

SUMMARY

Some embodiments of the present disclosure provide a method including a wearable device receiving a level of radiant energy, detecting a change in the received level of radiant energy, determining that the detected change in the received level of radiant energy is indicative of a predetermined pattern of received radiant energy, and responsively transmitting to an external reader an instruction that indicates that the wearable device has determined that the detected change in the received level of radiant energy is indicative of a predetermined pattern of received radiant energy.

Some embodiments of the present disclosure provide a method including a reader device transmitting to a wearable device radio frequency (RF) radiation, receiving from the wearable device one or more signals indicative of a change in a received level of radiant energy, determining that the change in the received level of radiant energy is indicative of a predetermined pattern of received radiant energy, and operating at least one external device.

Some embodiments of the present disclosure provide a system that includes a wearable device with an antenna, and a reader device. In some embodiments, the wearable device is configured to receive a level of radiant energy, detect a change in the received level of radiant energy, determine that the detected change is indicative of a predetermined pattern of received radiant energy, and in response to the determining, operate the antenna to transmit to the reader device an instruction that indicates that the wearable device has determined that the detected change in the received level of radiant energy is indicative of a predetermined pattern of received radiant energy. In some embodiments, the reader device is configured to receive the instruction from the wearable device, and in response to the receiving, operate at least one external device.

These as well as other aspects, advantages, and alternatives, will become apparent to those of ordinary skill in the art by reading the following detailed description, with reference where appropriate to the accompanying figures.

DETAILED DESCRIPTION

Figure 1:
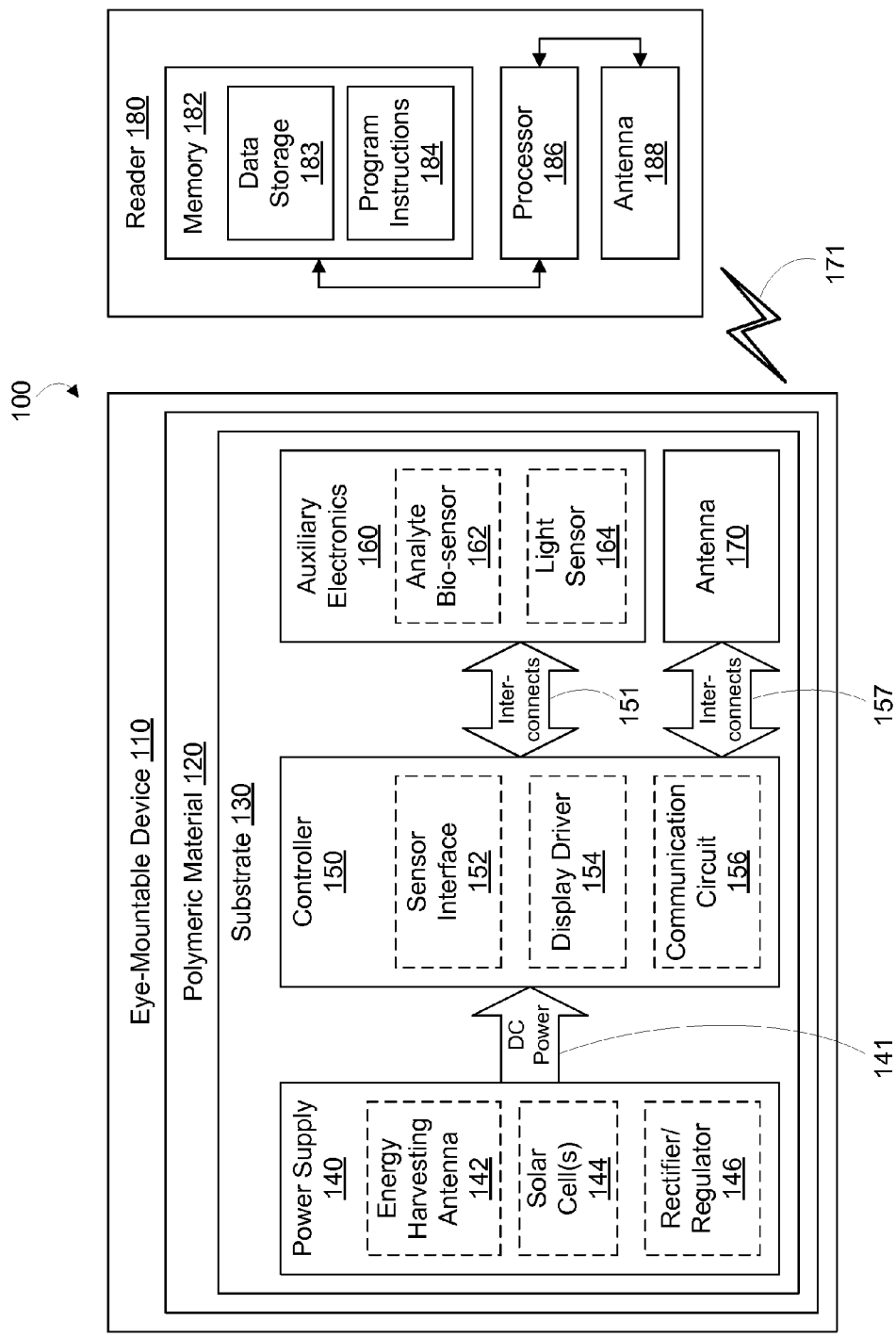
FIG. 1 is a block diagram of an example system that includes an eye-mountable device in wireless communication with an external reader, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device can include at least one sensor, control electronics, and an antenna embedded in a polymeric material formed to be contact mounted to an eye. The wearable device may be arranged to wirelessly communicate to an external reader via the antenna.

The polymeric material can be in the form of a round lens with a concave curvature configured to mount to a corneal surface of an eye. The electronics can be embedded on a substrate located near the periphery of the polymeric material to avoid interference with vision. In some examples, the electronics are entirely embedded within the contact lens material. For example, the antenna can be suspended in the lens material and situated such that it is less than about 10 micrometers from the polymeric surface configured to mount to the cornea.

The wearable device can be powered via radiated energy harvested by the antenna. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the control electronics from the harvested energy. The antenna can be arranged as a loop of conductive material with leads connected to the control electronics. In some embodiments, such a loop antenna can wirelessly communicate to an external reader by modifying the impedance of the loop antenna so as to modify backscatter radiation from the antenna.

In one embodiment, the sensor can be an electrochemical sensor configured for measuring analyte concentration in tear fluid. For instance, tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. In this embodiment, the sensor can be a part of a sensing platform that is arranged to measure one or more of these components and provide a convenient non-invasive platform to determine health-related parameters. For example, the sensing platform can be arranged to sense glucose and be used to measure glucose levels in diabetic patients.

The present disclosure provides an additional or alternative utilization for the wearable device. Disclosed herein is a technique utilizing a wearable device and an external reader for engaging in hands-free operation of an external device. In accordance with one example arrangement, the wearable device may be configured to recognize a user gesture (e.g., a blink, a head nod, a change of direction of a gaze, or any other similar body movement or pattern of body movements) as an intention to operate an external device in some way. Responsively, the wearable device may transmit a signal to the external reader indicating such an intention. The external reader may, as a result, operate an external device (e.g., a personal computer, tablet computer, cell phone, video game console, television, etc.) in some way.

In practice, a user gesture can impact the level of radiant energy (e.g., the signal strength of a signal) received at or transmitted by the wearable device. Thus, in some examples, when the level of radiant energy received at or transmitted by the wearable device changes in a predetermined way, the wearable device may determine that a particular user gesture has been performed and thereby interpret the change in the level of radiant energy as an instruction. In one example, the received radiant energy may be ambient light. In this example, the wearable device may include an ambient light sensor and associated control electronics configured to detect the amount of light incident upon the ambient light sensor. However in another example, the received radiant energy may be RF energy received from the external reader. In any case, the control electronics may be configured to recognize when the level of detected radiant energy at the wearable device changes in such a way that is indicative of a user gesture.

For instance, the wearable device may detect a blink when the level of detected radiant energy very briefly drops below a particular threshold level and then quickly returns to its previous level. Alternatively or additionally, the wearable device may detect a head nod when the level of detected radiant energy changes relatively slowly from a first level to a second level and then slowly returns to the first level. Still alternatively or additionally, the wearable device may detect a change of gaze when the level of detected radiant energy changes from a first level to a second level and then remains at the second level for at least a threshold period of time. Other ways of detecting user gestures based on the change of detected radiant energy levels are possible as well.

In some examples, the wearable device may detect just a single user gesture and, based on the detected user gesture, transmit to the external reader an instruction to operate an external device. Additionally or alternatively, the wearable device may detect some predetermined pattern of user gestures (e.g., three blinks in a row, two blinks and a head nod, etc.), and, based on the detected pattern of user gestures, transmit to the external reader an instruction to operate an external device.

In accordance with another arrangement, the external reader may be configured to recognize a user gesture based on signals transmitted by the wearable device. For instance, in some examples, the wearable device may be configured to transmit to the external reader an indication of the detected levels of radiant energy received at the wearable device. In the same way the wearable device itself may recognize user gestures as described above, the external reader may recognize user gestures based on detected changes in the levels of radiant energy received at and subsequently indicated by the wearable device. In response to detecting a single user gesture, or, in some cases, a pattern of user gestures, the external reader may operate an external device.

In accordance with another arrangement, an auxiliary device may be configured to recognize a user gesture based on inductive position sensing of the wearable device (e.g., an eye-mountable device) and responsively transmit to the external reader an indication of the user gesture. In one example, an inductive sensor may be positioned within a pair of glasses (or other head-mounted device). Movement of the eye-mountable device with respect to the inductive sensor, such as when the eye moves, may cause a change in the inductance of the inductive sensor. The auxiliary device may recognize when the inductance changes according to a predetermined pattern (such as an oscillating pattern or some other type of repeating pattern) and responsively transmit to the external reader an instruction to operate an external device. One type of repeating pattern may be indicative of the rapid eye movement stage of sleep. Accordingly, the intermediate device may transmit to the external reader an instruction to operate an external device, such a timer, a sleep-monitoring application on a computing device, or any other suitable external device.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, auxiliary electronics 160, and a communication antenna 170. The auxiliary electronics 160 are operated by the controller 150. The power supply 140 supplies operating voltages to the controller 150 and/or the auxiliary electronics 160. The antenna 170 is operated by the controller 150 to communicate information to and/or from the eye-mountable device 110. The antenna 170, the controller 150, the power supply 140, and the auxiliary electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the auxiliary electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc. to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the auxiliary electronics 160, and between the controller 150 and the antenna 170, respectively, can be formed by depositing suitable patterns of conductive materials on the substrate 130. A combination of resists, masks, and deposition techniques can be employed to pattern materials on the substrate 130. The substrate 130 can be a relatively rigid material, such as polyethylene terephthalate ("PET") or another material sufficient to structurally support the circuitry and/or electronics within the polymeric material 120. The eye-mountable device 110 can alternatively be arranged with a group of unconnected substrates rather than a single substrate. For example, the controller 150 and a light sensor or other auxiliary electronic component can be mounted to one substrate, while the antenna 170 is mounted to another substrate and the two can be electrically connected via the interconnects 157.

In some embodiments, auxiliary electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the auxiliary electronics 160 (and the substrate 130) can be positioned in the center region of the eye-mountable device 110. The auxiliary electronics 160 and/or substrate 130 can be substantially transparent to incoming visible light to mitigate interference with light transmission to the eye. Depending on the implementation of the wearable device, the auxiliary electronics 160 can include an ambient light sensor 164 that operates to detect the level of ambient light incident on the eye-mountable device 110. In implementations in which the eye-mountable device is used to detect analyte concentrations in tear fluid, the auxiliary electronics 160 may also include an analyte bio-sensor 162. Auxiliary electronics 160 may include other electronics as well.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and auxiliary electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and function as a low-pass filter.

The controller 150 is turned on when the DC supply voltage 141 is provided to the controller 150, and the logic in the controller 150 operates the auxiliary electronics 160 and the antenna 170. The controller 150 can include logic circuitry configured to operate the auxiliary electronics 160 so as to interact with a biological environment of the eye-mountable device 110 or take an ambient-light reading. The interaction could involve the use of one or more components, such an analyte bio-sensor 162, in auxiliary electronics 160 to obtain input from the biological environment.

In one example, the controller 150 includes a sensor interface module 152 that is configured to operate analyte bio-sensor 162. As mentioned above, the analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the auxiliary electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the auxiliary electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162 or light sensor 164), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162 or light sensor 164). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in eyeglasses, integrated in a piece of jewelry such as a necklace, earing, etc. or integrated in an article of clothing worn near the head, such as a hat, headband, etc. Thus, the external reader 180 could be provided as a head-mountable device.

Further, some embodiments of the system may include privacy controls which may be automatically implemented or controlled by the wearer of the device. For example, in embodiments in which a wearer's collected physiological parameter data and health state data are uploaded to a cloud computing network for trend analysis by a clinician, the data may be treated in one or more ways before it is stored or used, so that personally identifiable information is removed. For example, a wearer's identity may be treated so that no personally identifiable information can be determined for the wearer, or a wearer's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a wearer's preferences, or a wearer's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 2A:
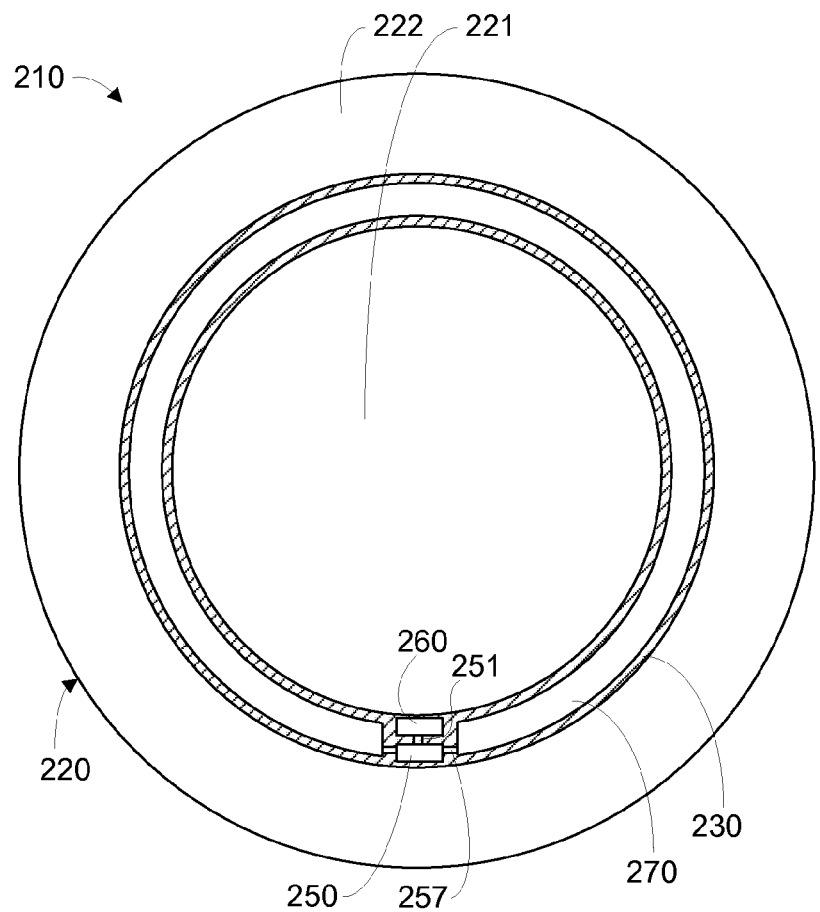
FIG. 2A is a bottom view of an example eye-mountable device, in accordance with an example embodiment.
Figure 2B:
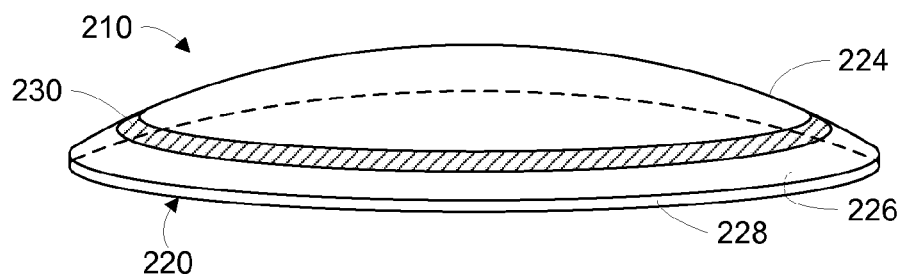
FIG. 2B is an aspect view of the example eye-mountable device shown in FIG. 2A, in accordance with an example embodiment.

FIG. 2A is a bottom view of an example eye-mountable electronic device 210. FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposing side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved out of the page, whereas the center region 221, near the center of the disk is curved in to the page.

A substrate 230 is embedded in the polymeric material 220. The substrate 230 can be embedded to be situated along the outer periphery 222 of the polymeric material 220, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a flat, circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 270, controller 250, and auxiliary electronics 260 are disposed on the embedded substrate 230. The controller 250 can be a chip including logic elements configured to operate the auxiliary electronics 260 and the loop antenna 270. The controller 250 is electrically connected to the loop antenna 270 by interconnects 257 also situated on the substrate 230. Similarly, the controller 250 is electrically connected to the auxiliary electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the auxiliary electronics module 260 is mounted to a side of the substrate 230 facing the concave surface 226. Where the auxiliary electronics module 260 includes an analyte bio-sensor, for example, mounting such a bio-sensor on the substrate 230 to be close to the concave surface 226 allows the bio-sensor to sense analyte concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instance, loop antenna 270 can have a cutout to allow room for the controller 250 and auxiliary electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and auxiliary electronics 260. Interconnects between the ends of such a wound antenna (e.g., the antenna leads) can be passed through the substrate 230 to the controller 250.

Figure 2C:
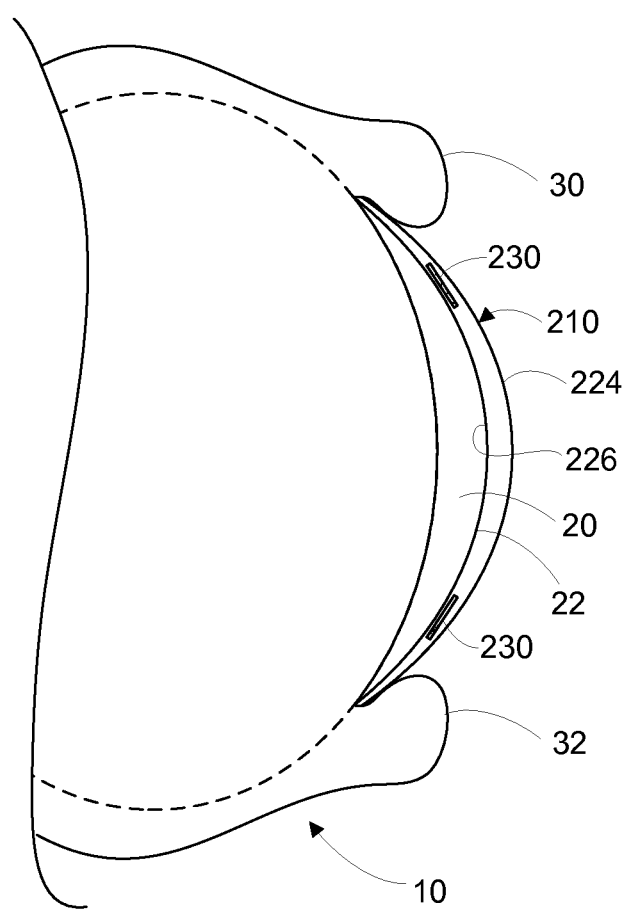
FIG. 2C is a side cross-section view of the example eye-mountable device shown in FIGS. 2A and 2B while mounted to a corneal surface of an eye, in accordance with an example embodiment.

FIG. 2C is a side cross-section view of the example eye-mountable electronic device 210 while mounted to a corneal surface 22 of an eye 10. It is noted that relative dimensions in FIG. 2C may not necessarily be to scale, but are rendered for purposes of explanation only in describing the arrangement of the example eye-mountable electronic device 210. Some aspects are exaggerated to allow for illustration and facilitate explanation.

As depicted, the eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 may distribute a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer (along the concave surface 226) and an outer layer (along the convex layer 224). The tear film layers can be about 10 micrometers in thickness and together account for about 10 microliters. In some embodiments, the eye-mountable device 210 can also be held over the eye in part by vacuum forces against corneal surface 22 due to the concave curvature of the eye-facing concave surface 226.

As shown in the cross-sectional view in FIG. 2C, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234.

III. Example Hands-Free Operation

Figure 3:
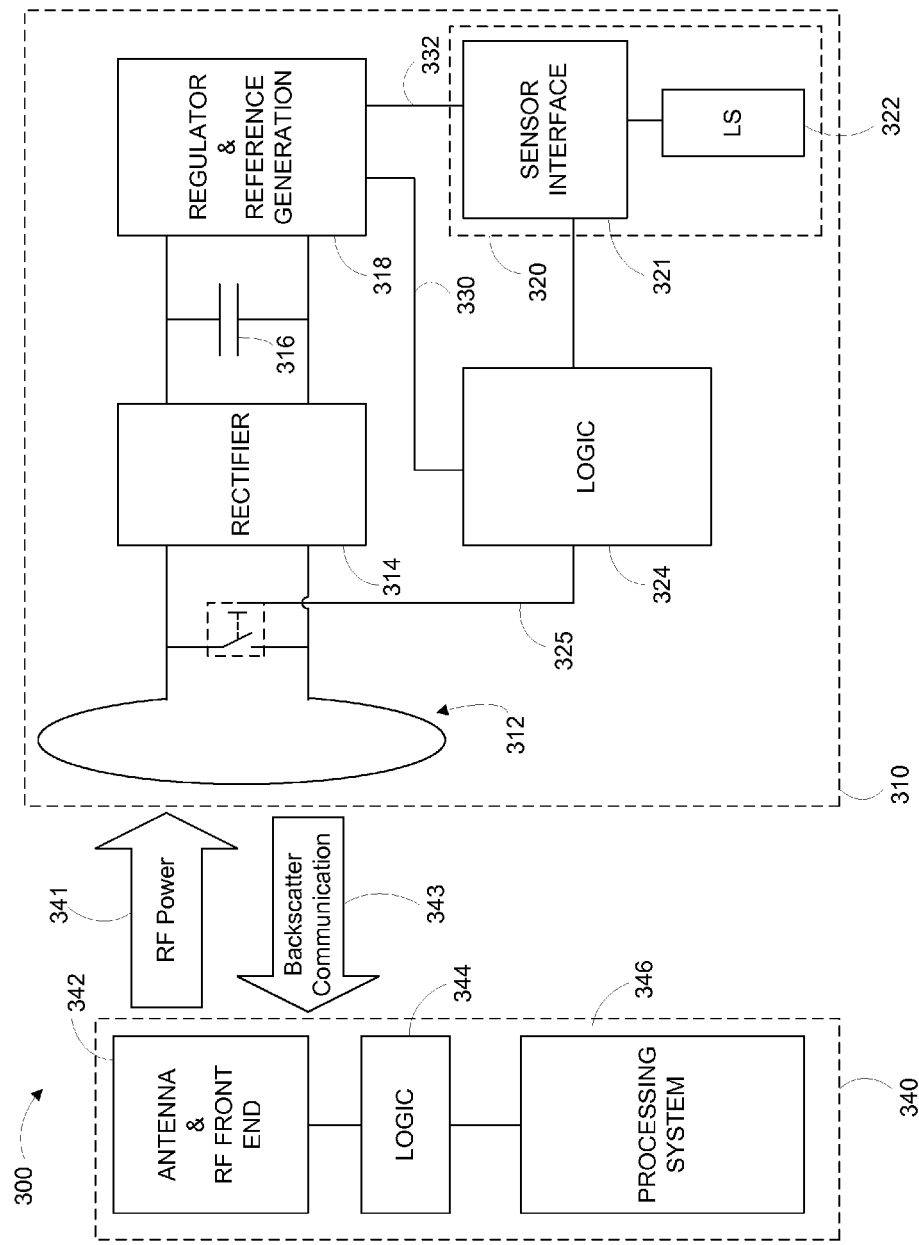
FIG. 3 is a functional block diagram of an example system, in accordance with an example embodiment.

FIG. 3 is a functional block diagram of a system 300 for recognizing a user gesture or pattern of user gestures. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes a sensor platform 320 with a light sensor 322 driven by a sensor interface 321.

The eye-mountable device 310 also includes hardware logic 324 for communicating sensor measurements from the sensor 320 to the external reader 340 by modulating (325) the impedance of the antenna 312. Similar to the eye-mountable devices 110, 210 discussed above in connection with FIGS. 1 and 2, the eye-mountable device 310 can include a mounting substrate embedded within a polymeric material configured to be mounted to an eye. The sensor platform 320 can be situated on a mounting surface of such a substrate proximate the surface of the eye (e.g., corresponding to the auxiliary electronics 260 on the inward-facing side 232 of the substrate 230) to measure the light levels incident on the eye-mountable device 310.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. Thee regulator 318 receives the filtered DC voltage and outputs both a digital supply voltage 330 to operate the hardware logic 324 and an analog supply voltage 332 to operate the sensor 320. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324.

In some embodiments, the eye-mountable device 310 is configured to recognize a user gesture (e.g., a blink, head nod, change of gaze, or other similar body movement or pattern of body movements) based on a detected change of radiant energy received via the light sensor 322 or the antenna 312. In one example, certain changes in the level of ambient light or the level of RF power 341 received from the reader 340 may be indicative of particular movements of the eye-mountable device 310. For instance, when the level of radiant energy received (via the light sensor 322 or the antenna 312) drops below a threshold level and then relatively quickly returns to at or near its previous level, this change may be indicative of a blink. Additionally, when the level of radiant energy received changes relatively slowly from a first level to a second level and then relatively slowly returns to at or near the first level, this change may be indicative of a nod of the head. Still additionally, when the level of radiant energy received changes from a first level to a second level and then remains at the second level for at least a threshold period of time, this change may be indicative of a change of gaze. Other changes in the levels of received radiant energy may be indicative of other user gestures as well.

Thus, in accordance with one arrangement, the logic 324 is configured to monitor the levels of radiant energy received via the sensor platform 320 and antenna 312 to detect changes in these levels and to determine whether the detected changes are indicative of a predetermined pattern. To measure the level of ambient light, logic 324 senses the DC voltage generated at light sensor 322. To measure the level of RF radiation received from the external reader 340, logic 324 senses the filtered DC voltage across capacitor 316. When the logic 324 determines that a detected change is indicative of a predetermined pattern, the logic 324 may cause the eye-mountable device to communicate this detection to the external reader 340 so that the external reader 340 can operate an external device.

For instance, the eye-mountable device may communicate back to the external reader 340 via backscatter radiation 343 from the antenna 312. Upon determining that a detected change in the received level of radiant energy is indicative of a predetermined pattern, the logic 324 may modulate (325) the impedance of the antenna 312 in such a way as to indicate this determination to reader 340. The antenna impedance and/or change in antenna impedance is detected by the external reader 340 via the backscatter signal 343.

The external reader 340 can include an antenna front end 342 and logic 344 to decode the information indicated by the backscatter signal 343 and provide digital inputs to a processing system 346. The external reader 340 associates the backscatter signal 343 with a particular user gesture. The processing system 346 can then operate one or more external devices (not shown) in accordance with the type of detected movement. By way of example, the processing system can utilize antenna front end 342 to wirelessly transmit a signal to and thereby operate a personal computer, tablet computer, cell phone, video game console, television, or other external device.

In accordance with another arrangement, logic 324 is configured to communicate to the external reader the levels of radiant energy received at the eye-mountable device 310 and the logic 344 included in the external reader is configured to carry out the determination of whether the levels of received radiant energy are indicative of a predetermined pattern. In this arrangement, the logic 324 modulates the impedance of the antenna 312 in such a way as to indicate the levels of radiant energy received at the eye-mountable device. And the logic 344 decodes the information indicated by the backscatter signal 343 to read the levels of radiant energy received by the eye-mountable device 310. When the logic 344 determines that the levels of received radiant energy have changed in accordance with a predetermined pattern, the logic 344 provides digital inputs to processing system 346, which can then operate one or more external devices.

In accordance with still another arrangement, the external reader 340 is configured to periodically poll the eye-mountable device by transmitting to the eye-mountable device RF signals 341. In response to receiving the RF signals 341, the logic 324 may set the impedance of the antenna 312 so as to transmit to the external reader 340 a backscatter scatter 343 of a set power level. The external reader may then monitor the power levels at which it receives the backscatter signals from the eye-mountable device to determine whether any changes detected in the received power levels are indicative of a predetermined pattern. When the external reader determines that the levels of received radiant energy have changed in accordance with a predetermined pattern, the logic 344 may provide digital inputs to processing system 346, which can then operate one or more external devices.

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the logic 324 packaged together in a single chip or controller module.

Whereas the device described herein is described as comprising the eye-mountable device 110 and/or the eye-mountable device 310, the device could comprise other devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein.

Figure 4:
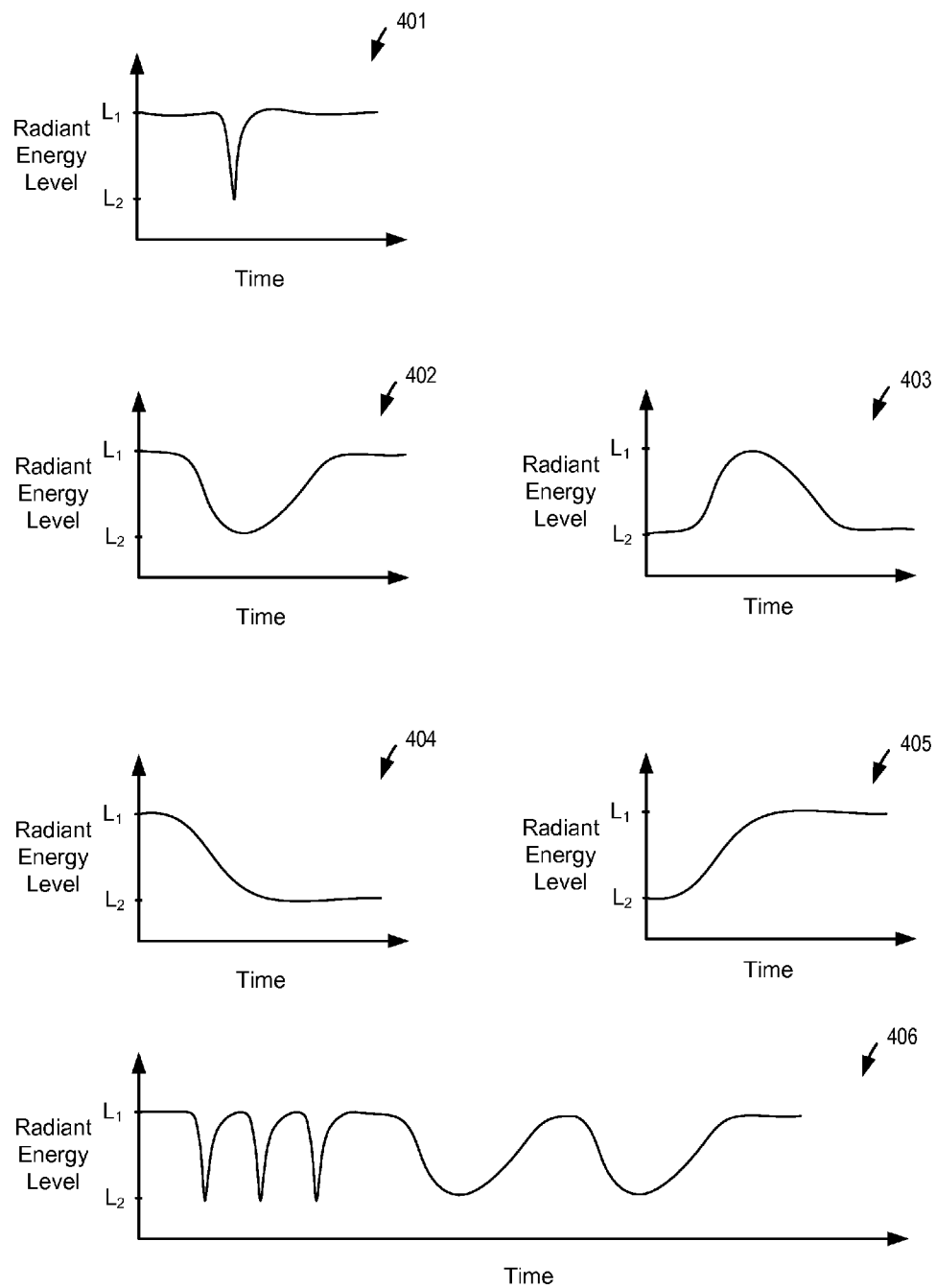
FIG. 4 depicts graphs illustrating example patterns of received radiant energy, in accordance with example embodiments.

FIG. 4 shows six graphs depicting example patterns of received radiant energy that may be indicative of user gestures. The example patterns of received radiant energy may be received at the eye-mountable device 310 via the light sensor 322 or the antenna 312. Alternatively, the example patterns of received radiant energy may be received at the external reader via backscatter signals sent by the eye-mountable device. The depicted graphs are merely examples, and in other embodiments, other patterns of received radiant energy are possible as well.

Graph 401 depicts an example pattern of received radiant energy that may be indicative of a blink. In graph 401, the received radiant energy level drops from a level $L_1$ to a level $L_2$ and then relatively quickly returns to at or near the original level $L_1$. The eye-mountable device 310 and/or the external reader 340 may determine that a given pattern of received radiant energy is indicative of a blink when the received radiant energy level drops from a first level to at or below a threshold level and then returns to at or near the original first level within a threshold period of time. In one example the threshold level is a level that is about 80% lower than the first level, and the threshold period of time is about 0.5 seconds. However, in other examples, other values are possible.

Graphs 402 and 403 depict example patterns of received radiant energy that may be indicative of a head shake or nod. In graph 402, the received radiant energy level drops from a level $L_1$ to a level $L_2$, and then relatively slowly returns to at or near the original level $L_1$. In graph 403, the received radiant energy level rises from a level $L_2$ to a level $L_1$ and then relatively slowly returns to at or near the original level. The eye-mountable device 310 and/or the external reader 340 may determine that a given pattern of received radiant energy is indicative of a head shake or nod when the received radiant energy level changes from a first level to a second level and then returns to at or near the original first level after at least a threshold period of time. In one example the second level is a level that is at least 20% higher or at least 20% lower than the first level, and the threshold period of time is about 1.0 seconds. However, in other examples, other values are possible.

Graphs 404 and 405 depict example patterns of received radiant energy that may be indicative of a change of gaze. In graph 404, the received radiant energy level drops from a level $L_1$ to a level $L_2$, and then remains at or near level $L_2$ for at least a threshold period of time. In graph 405, the received radiant energy level rises from a level $L_2$ to a level $L_1$ and then remains at or near level $L_1$ for at least a threshold period of time. The eye-mountable device 310 and/or the external reader 340 may determine that a given pattern of received radiant energy is indicative of a change of gaze when the received radiant energy level changes from a first level to a second level and then remains at the second level for at least a threshold period of time. In one example the threshold period of time 1.0 seconds. However, in other examples, other values are possible.

Graph 406 depicts an example pattern of received radiant energy that may be indicative of a combination of user gestures. In graph 406, the received radiant energy exhibits characteristics of three blinks in a row followed by characteristics of two head shakes or nods. The eye-mountable device 310 and/or the external reader 340 may determine that a given pattern of received radiant energy is indicative of a combination of user gestures when the received radiant energy level exhibits a combination of two or more of the patterns described with respect to graphs 401-405 within a threshold period of time. In one example the threshold period of time 5.0 seconds. However, in other examples, other values are possible.

Figure 5A:
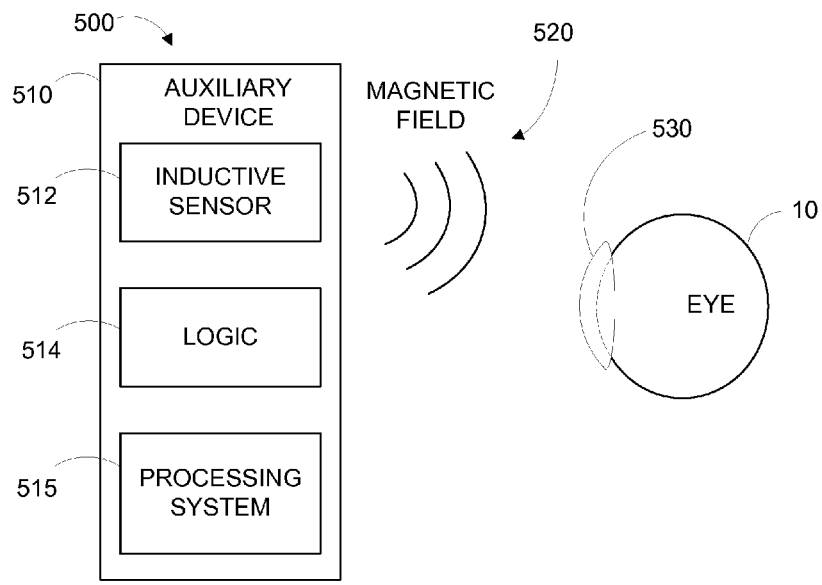
FIG. 5A is a functional block diagram of an example system in accordance with an example embodiment.
Figure 5B:
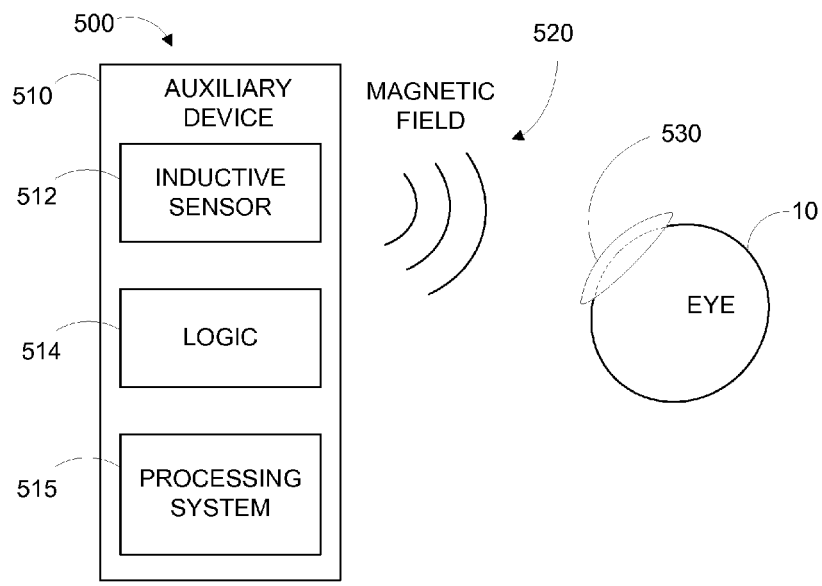
FIG. 5B is a functional block diagram of an example system in accordance with an example embodiment.

FIGS. 5A and 5B depict an additional arrangement configured to detect the movement of the eye-mountable device. As depicted, FIGS. 5A and 5B show a system 500 with an auxiliary device 510 and an eye-mountable device 530 mounted on an eye 10. The eye-mountable device 530 can be similar to the eye-mountable devices 110, 210, 310 discussed in connection with FIGS. 1-3 above and generally includes a sensor and antenna embedded within a polymeric material configured to be contact-mounted to an eye.

Generally, the auxiliary device may be any device worn, carried, or otherwise positioned near the eye-mountable device 530. In some embodiments, the auxiliary device is integrated within a pair of eyeglasses, a piece of jewelry such as a necklace, earing, etc. or integrated in an article of clothing worn near the head, such as a hat, headband, etc. Thus, the auxiliary device could be a head-mountable device.

The auxiliary device 510 includes an inductive sensor 512, logic 514, and a processing system 515. In accordance with one embodiment, the inductive sensor operates to detect the movement of the metal portions of eye-mountable device 530 (e.g., the sensor and the antenna) by emitting a magnetic field 520 and measuring changes. By way of example, the system 500 may be arranged to detect when the eye 10 rotates from its position in FIG. 5A to its position in FIG. 5B. However, the system 500 may be arranged to detect other patterns of movement as well.

More specifically, movement of the metal portions of eye-mountable device 530 in the presence of the magnetic field 520 may disturb and change the magnetic field 520 and thus the inductance in the inductive sensor 512. As such, the inductive sensor 512 in conjunction with logic 514 is operable to detect this change in inductance and determine whether the change is indicative of a predetermined pattern. When the inductance change is indicative of a predetermined pattern, the logic 514 may provide digital inputs to processing system 515, which in turn may operate one or more other components (not shown) of auxiliary device 510 to wireless transmit a signal to the external reader, which in turn may operate a personal computer, tablet computer, cell phone, video game console, television, or other external device.

In one example, a certain pattern of changed inductance in the inductive sensor may be indicative of the movements of eye 10 associated with Rapid Eye Movement (REM) stage sleep. In this example, when the auxiliary device detects this type of pattern, the auxiliary device may alert the external reader to transmit signals to nearby external devices to initiate one or more sleep-related functions, such as dimming lights, reducing volume, and/or setting an alarm. However, other patterns of eye movement may indicate to the auxiliary device and external reader to carry out other functions.

Figure 6:
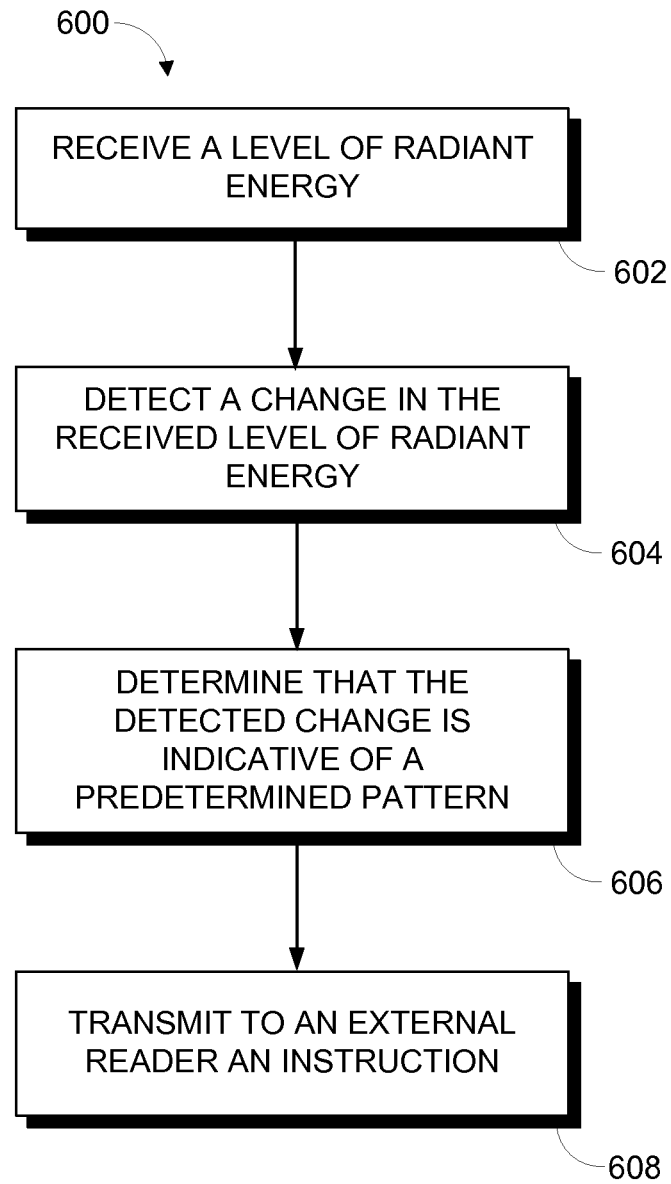
FIG. 6 is a flowchart of an example hands-free operation process, in accordance with an example embodiment.
Figure 7:
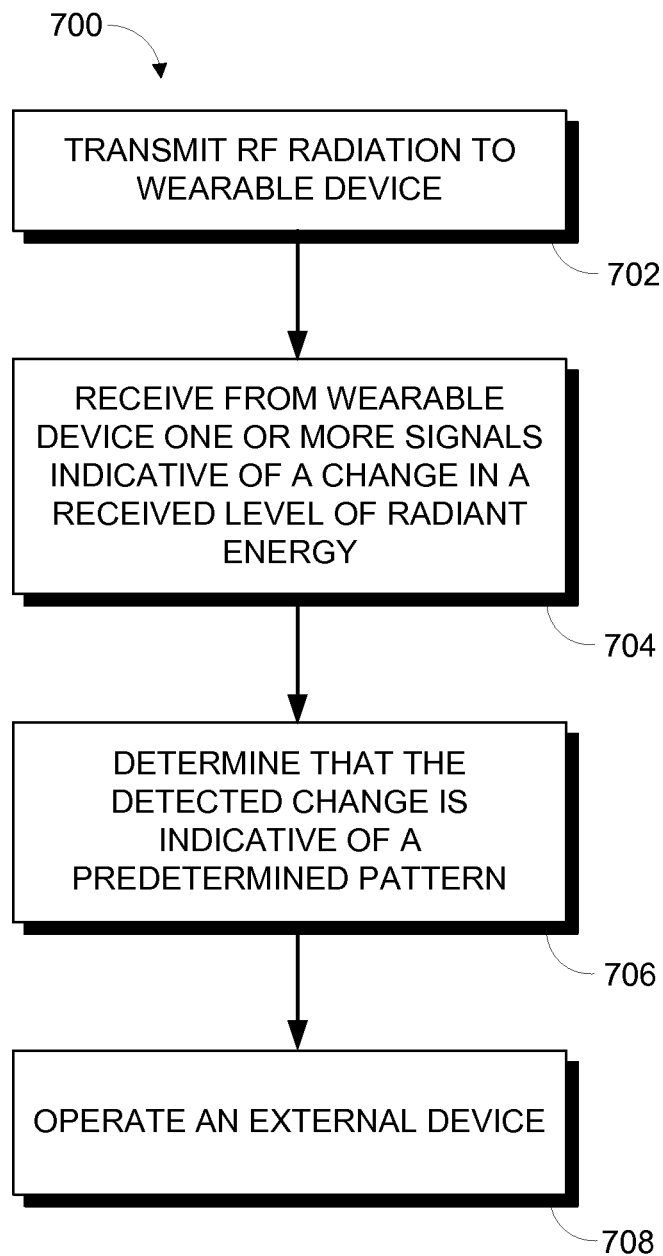
FIG. 7 is a flowchart of an example hands-free operation process, in accordance with an example embodiment.

FIGS. 6 and 7 are flowcharts of example methods 600 and 700 that could be used for hands-free operation of an external device. The example methods 600 and 700 may include one or more operations, functions, or actions, as depicted by one or more of blocks 602, 604, 606, 608, 702, 704, 706, and/or 708, each of which may be carried out by any of the systems described by way of FIGS. 1-5; however, other configurations could be used.

Furthermore, those skilled in the art will understand that the flowcharts described herein illustrate functionality and operation of certain implementations of example embodiments. In this regard, each block of each flow diagram may represent a module, a segment, or a portion of program code, which includes one or more instructions executable by a processor (e.g., processor 186 described above with respect to reader 180) for implementing specific logical functions or steps in the process. The program code may be stored on any type of computer readable medium (e.g., computer readable storage medium or non-transitory media, such as data storage 183 described above with respect to reader 180), for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

The method 600 begins at block 602, in which an eye-mountable device receives a level of radiant energy. For example, as described above, the eye-mountable device may receive a level of light via a light sensor or the eye-mountable device may receive a level of RF radiation from an external reader. However, other ways to receive radiant energy are possible as well.

Continuing at block 604, the eye-mountable device detects a change in the received level of radiant energy. For example, the received level of radiant energy may change from a first level to a second level and then return to the first level. However, as described above, other changes in the received level of radiant energy are possible as well.

At block 606, the eye-mountable device determines that the detected change is indicative of a predetermined pattern of received radiant energy. For example, as described above, the eye-mountable device may determine that the radiant energy level dropped from a first level to at or below a threshold level and then returned to at or near the original first level within a threshold period of time. Accordingly, the eye-mountable device may recognize the change as being indicative of a blink. However, as also described above, other patterns are possible as well.

Finally, at block 608, the eye-mountable device transmits to an external reader an instruction that indicates that the eye-mountable device has detected a change in the received level of radiant energy that is indicative of a predetermined pattern. In response, the reader device may operate one or more external devices based on the predetermined pattern. In one example, the reader operates an external device by wirelessly transmitting one or more signals to a personal computer, tablet computer, cell phone, video game console, television, and/or some other computing device. The one or more signals may cause the external device to power on, power off, adjust volume, change a channel, change some other setting, or manipulate the external device in some other way. Other examples of operating an external device are possible as well.

The method 700 begins at block 702, in which an external reader transmits RF radiation to a wearable device, such as an eye-mountable device. As described above, the RF radiation may be used to power the wearable device.

Continuing at block 704, the external reader receives from the wearable device, in response to transmitting the RF radiation, one or more signals that are indicative of a change in the received level of radiant energy. In one example, the received signals indicate levels of radiant energy received at the wearable device over a period of time. As described above, such radiant energy may be light energy received via a light sensor on the wearable device or the radiant energy may be RF radiation previously received from the external reader. Thus, the signals indicate a change in the received level of radiant energy at the wearable device.

In another example, the received signals are reference signals transmitted from the wearable device at the same power level but received at the external reader at different power levels. Thus, the signals indicate a change in the received level of radiant energy at the external reader itself. However, other ways to indicate a change in a received level of radiant energy are possible as well.

Continuing at block 706, the external reader determines that the detected change is indicative of a predetermined pattern of received radiant energy. For example, as described above, the external reader may determine that the radiant energy level dropped from a first level to at or below a threshold level and then returned to at or near the original first level within a threshold period of time. Accordingly, the eye-mountable device may recognize the change as being indicative of a blink. However, as also described above, other patterns are possible as well.

Finally, at block 708, in response to determining that the detected change is indicative of a predetermined pattern, the external reader operates one or more external devices based on the predetermined pattern. As described above, in one example, the external reader operates an external device by wirelessly transmitting one or more signals to a personal computer, tablet computer, cell phone, video game console, television, and/or some other computing device. The one or more signals may cause the external device to power on, power off, adjust volume, change a channel, change some other setting, or manipulate the external device in some other way. Other examples of operating an external device are possible as well.

Figure 8:
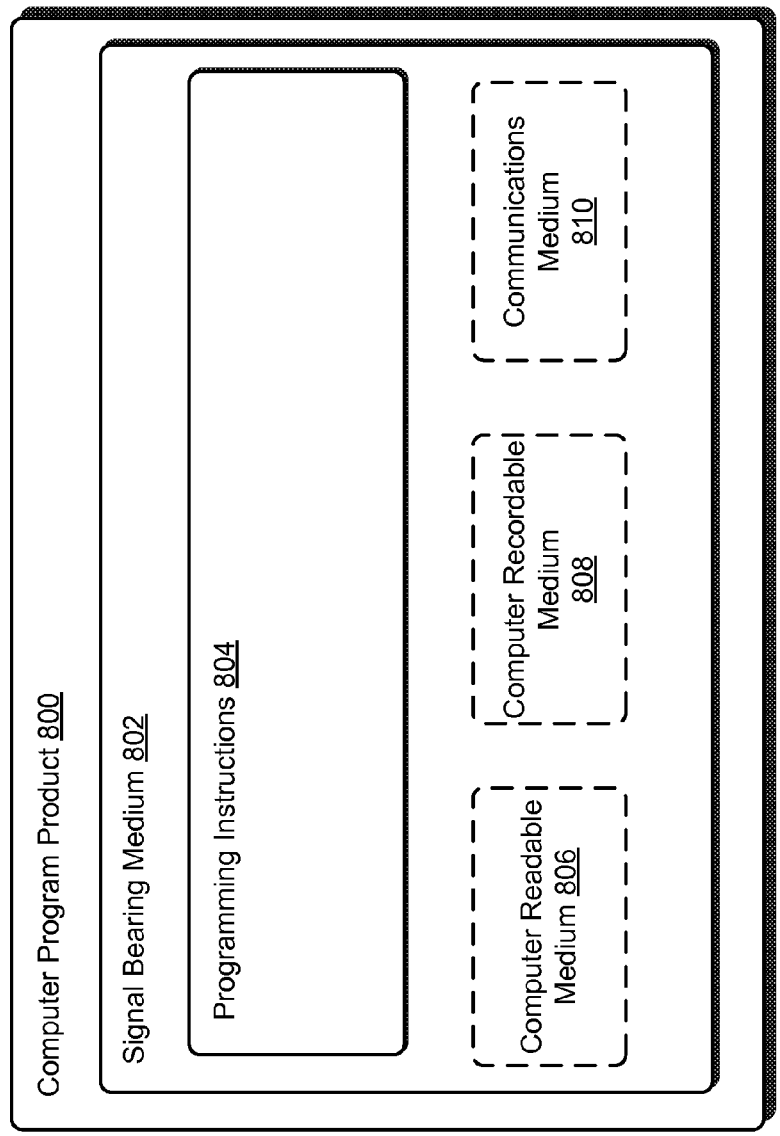
FIG. 8 depicts a computer-readable medium configured, in accordance with an example embodiment.

FIG. 8 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 184 stored on the memory storage 182 of the external reader 180 of the system 100). FIG. 8 is a schematic illustrating a conceptual partial view of an example computer program product that includes a computer program for executing a computer process on a computing device, arranged according to at least some embodiments presented herein.

In one embodiment, the example computer program product 800 is provided using a signal bearing medium 802. The signal bearing medium 802 may include one or more programming instructions 804 that, when executed by one or more processors may provide functionality or portions of the functionality described above with respect to FIGS. 1-7. In some examples, the signal bearing medium 802 can be a computer-readable medium 806, such as, but not limited to, a hard disk drive, a Compact Disc (CD), a Digital Video Disk (DVD), a digital tape, memory, etc. In some implementations, the signal bearing medium 802 can be a computer recordable medium 808, such as, but not limited to, memory, read/write (R/W) CDs, R/W DVDs, etc. In some implementations, the signal bearing medium 802 can be a communications medium 810, such as, but not limited to, a digital and/or an analog communication medium (e.g., a fiber optic cable, a waveguide, a wired communications link, a wireless communication link, etc.). Thus, for example, the signal bearing medium 802 can be conveyed by a wireless form of the communications medium 810.

The one or more programming instructions 804 can be, for example, computer executable and/or logic implemented instructions. In some examples, a computing device such as the processor-equipped external reader 180 of FIG. 1 is configured to provide various operations, functions, or actions in response to the programming instructions 804 conveyed to the computing device by one or more of the computer readable medium 806, the computer recordable medium 808, and/or the communications medium 810.

The non-transitory computer readable medium 806 can also be distributed among multiple data storage elements, which could be remotely located from each other. The computing device that executes some or all of the stored instructions could be an external reader, such as the reader 180 illustrated in FIG. 1, or another mobile computing platform, such as a smartphone, tablet device, personal computer, etc. Alternatively, the computing device that executes some or all of the stored instructions could be remotely located computer system, such as a server.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
a wearable device receiving from an external reader a level of radiant energy;
the wearable device detecting a change in the received level of radiant energy;
the wearable device determining that the detected change in the received level of radiant energy is indicative of a predetermined pattern of received radiant energy, wherein determining that the detected change in the received level of radiant energy is indicative of a predetermined pattern of received radiant energy comprises determining that the detected change in the received level of radiant energy is indicative of at least one body movement; and
in response to the determining, the wearable device transmitting to the external reader an instruction that indicates that the wearable device has determined that the detected change in the received level of radiant energy is indicative of a predetermined pattern of received radiant energy.

2. The method of claim 1,
wherein receiving a level of radiant energy comprises receiving a level of light incident on a light detector associated with the wearable device.

3. The method of claim 1,
wherein receiving a level of radiant energy comprises receiving a level of radio frequency (RF) radiation from the external reader.

4. The method of claim 1, wherein determining that the detected change in the received level of radiant energy is indicative of a predetermined pattern of received radiant energy comprises determining that some combination of two or more of the following has occurred:
the received level of radiant energy has, within a threshold period of time, changed from a first level to a second level and then returned to at or near the first level,
the received level of radiant energy has changed from a first level to a second level and then remained at the second level for at least a threshold period of time, and
the received level of radiant energy has, over a period of time greater than or equal to a threshold period of time, changed from a first level to a second level and then returned to at or near the first level.

5. The method of claim 1, wherein the wearable device transmitting to an external reader an instruction causes the external reader to transmit an instruction to at least one external device.

6. The method of claim 1, wherein the at least one body movement comprises a blink, a nod, or a change of gaze.

7. The method of claim 6, wherein the at least one body movement comprises a blink, wherein determining that the detected change in the received level of radiant energy is indicative of a blink comprises:
determining that the received level of radiant energy has, within a threshold period of time, changed from a first level to a second level and then returned to at or near the first level.

8. The method of claim 6, wherein the at least one body movement comprises a change of gaze, wherein determining that the detected change in the received level of radiant energy is indicative of a change of gaze comprises:
determining that the received level of radiant energy has changed from a first level to a second level and then remained at the second level for at least a threshold period of time.

9. The method of claim 6, wherein the at least one body movement comprises a nod, wherein determining that the detected change in the received level of radiant energy is indicative of a nod comprises:
determining that the received level of radiant energy has, over a period of time greater than or equal to a threshold period of time, changed from a first level to a second level and then returned to at or near the first level.

10. A method comprising:
a reader device transmitting to a wearable device radiant energy;
in response to the transmitting, the reader device receiving from the wearable device one or more signals indicative of a change in a received level of the radiant energy from the reader device;
the reader device determining that the change in the received level of the radiant energy from the reader device is indicative of a predetermined pattern of received radiant energy, wherein determining that the change in the received level of the radiant energy from the reader device is indicative of a predetermined pattern of received radiant energy comprises determining that the change in the received level of the radiant energy from the reader device is indicative of at least one body movement; and
in response to the determining, the reader device operating at least one external device.

11. The method of claim 10,
wherein the reader device receiving from the wearable device one or more signals indicative of a change in a received level of the radiant energy from the reader device comprises:
the reader device receiving from the wearable device one or more signals indicative of levels of the radiant energy from the reader device received at the wearable device; and
based on the one or more signals, the reader device detecting a change in the received level of the radiant energy from the reader device at the wearable device.

12. The method of claim 11,
wherein the levels of the radiant energy from the reader device received at the wearable device comprise levels of light incident on a light detector associated with the wearable device.

13. The method of claim 11,
wherein the levels of the radiant energy from the reader device received at the wearable device comprise levels of radio frequency (RF) radiation received from the reader device.

14. The method of claim 10,
wherein the reader device receiving from the wearable device one or more signals indicative of a change in a received level of the radiant energy from the reader device comprises:
the reader device receiving from the wearable device a level of backscatter radiation; and
the reader device detecting a change in the received level of backscatter radiation.

15. The method of claim 10, wherein determining that the change in the received level of the radiant energy from the reader device is indicative of a predetermined pattern of received radiant energy comprises determining that some combination of two or more of the following has occurred:
- the received level of the radiant energy from the reader device has, within a threshold period of time, changed from a first level to a second level and then returned to at or near the first level,
- the received level of the radiant energy from the reader device has changed from a first level to a second level and then remained at the second level for at least a threshold period of time, and
- the received level of the radiant energy from the reader device has, over a period of time greater than or equal to a threshold period of time, changed from a first level to a second level and then returned to at or near the first level.

16. The method of claim 10, wherein the at least one body movement comprises a blink, a nod, or a change of gaze.

17. The method of claim 16, wherein the at least one body movement comprises a blink, wherein determining that the change in the received level of the radiant energy from the reader device is indicative of a blink comprises:
- determining that the received level of the radiant energy from the reader device has, within a threshold period of time, changed from a first level to a second level and then returned to at or near the first level.

18. The method of claim 16, wherein the at least one body movement comprises a change of gaze, wherein determining that the change in the received level of the radiant energy from the reader device is indicative of a change of gaze comprises:
- determining that the received level of the radiant energy from the reader device has changed from a first level to a second level and then remained at the second level for at least a threshold period of time.

19. The method of claim 16, wherein the at least one body movement comprises a nod, wherein determining that the change in the received level of the radiant energy from the reader device is indicative of a nod comprises:
- determining that the received level of the radiant energy from the reader device has, over a period of time greater than or equal to a threshold period of time, changed from a first level to a second level and then returned to at or near the first level.

20. A system comprising:
a wearable device comprising an antenna; and
a reader device,
wherein the wearable device is configured to:
- receive a level of radiant energy from the reader device;
- detect a change in the received level of radiant energy;
- determine that the detected change is indicative of a predetermined pattern of received radiant energy, wherein determining that the detected change in the received level of radiant energy is indicative of a predetermined pattern of received radiant energy comprises determining that the detected change in the received level of radiant energy is indicative of at least one body movement; and
- in response to the determining, operate the antenna to transmit to the reader device an instruction that indicates that the wearable device has determined that the detected change in the received level of radiant energy is indicative of a predetermined pattern of received radiant energy, and wherein the reader device is configured to:
- receive the instruction from the wearable device; and
- in response to the receiving, operate at least one external device.

21. The system of claim 20, further comprising:
an auxiliary device comprising an inductive sensor, wherein the auxiliary device is configured to:
- determine a level a level of inductance of the inductive sensor based on the proximity of the wearable device to the auxiliary device;
- detect a change in the level of inductance;
- determine that the determined change is indicative of a predetermined pattern of determined inductance; and
- transmit to the reader device an auxiliary instruction that indicates that the auxiliary device has determined that the detected change in the level of inductance is indicative of a predetermined pattern of determined inductance, and wherein the reader device is further configured to:
- receive the auxiliary instruction from the auxiliary device; and
- in response to the receiving, operate at least one external device.

22. The system of claim 20, wherein the wearable device is configured to determine that the detected change is indicative of a predetermined pattern of received radiant energy comprises determining that some combination of two or more of the following has occurred:
- the received level of radiant energy has, within a threshold period of time, changed from a first level to a second level and then returned to at or near the first level,
- the received level of radiant energy has changed from a first level to a second level and then remained at the second level for at least a threshold period of time, and
- the received level of radiant energy received has, over a period of time greater than or equal to a threshold period of time, changed from a first level to a second level and then returned to at or near the first level.

* * * * *